United States Patent [19]

Johnson

[11] 4,324,200

[45] Apr. 13, 1982

[54] METHOD AND APPARATUS FOR GROWING HYDROZOA

[75] Inventor: E. Marshall Johnson, Philadelphia, Pa.

[73] Assignee: Rockhill Enterprises, Philadelphia, Pa.

[21] Appl. No.: 119,658

[22] Filed: Feb. 8, 1980

[51] Int. Cl.³ .......................................... A01K 61/00
[52] U.S. Cl. .......................................... 119/2; 119/3
[58] Field of Search .................................. 119/2, 3, 4

[56] References Cited

U.S. PATENT DOCUMENTS

| | | | |
|---|---|---|---|
| 2,994,513 | 7/1960 | Keely | 119/3 |
| 3,025,831 | 3/1962 | Berardi | 119/2 |
| 3,116,712 | 1/1964 | Ogden et al. | 119/3 |
| 3,166,043 | 1/1965 | Castillo | 119/3 |
| 3,377,991 | 4/1968 | Rubert | 119/3 X |
| 3,387,587 | 6/1968 | Kelley et al. | 119/2 |
| 3,526,209 | 9/1970 | Budge | 119/4 |
| 3,967,585 | 7/1976 | Monaco | 119/2 |
| 4,226,210 | 10/1980 | Lockwood et al. | 119/4 |
| 4,250,835 | 2/1981 | Dugan et al. | 119/2 |
| 4,267,798 | 5/1981 | Collins | 119/3 |

Primary Examiner—Hugh R. Chamblee
Attorney, Agent, or Firm—Woodcock, Washburn, Kurtz, Mackiewicz & Norris

[57] ABSTRACT

A system and apparatus for the growth of hydrozoa, e.g. hydra is disclosed which comprises a tank having a fluid medium therein for the growth of the hydra and pump means for recycling and filtering the medium. Temperature control and oxygenation apparatus may also be provided. In a preferred embodiment, the tank has a roughened surface for the attachment of hydra thereto so as to form a stable resident population of hydra. When it is desired to remove a quantity of hydra for an experiment, they can be dislodged from the surface by means of, e.g., a razor blade and collected, by means of the recycle current, on a net disposed in the current path.

32 Claims, 4 Drawing Figures

METHOD AND APPARATUS FOR GROWING HYDROZOA

FIELD OF THE INVENTION

This invention relates to methods and apparatus for the efficient production of hydrozoa. More particularly, the invention relates to a tank and associated equipment in which hydra may be grown for laboratory experiments in a much more stable, uniform, healthy and economic fashion than was possible in the prior art.

BACKGROUND OF THE INVENTION

The family hydrozoa has a genus, Hydra, which have been known for many years to be useful in laboratory experiments. Hydra are small fresh water coelenterates which are essentially carnivorous and which reproduce both asexually and sexually, depending on the temperature and other environmental factors of the fluid medium in which they are contained. They comprise a body, having a foot or member adapted for attachment of the creature to a surface at one end of living the body, and a plurality (on the average 6.3) of food gathering tentacles at the other end. They eat by grasping a small portion of living food matter from the fluid medium with the tentacles and pushing it towards their mouth which is more or less at the juncture of the tentacles.

The use of hydra in various sorts of laboratory experiments has been a common practice for many years. However, there has not been developed a labor-efficient method for their uniform production. Rather, hydra have been grown in individual laboratory dishes or bowls. Inasmuch as hydra must be almost daily cleansed and fed, the use of such dishes for their containment has led to certain problems. In particular, laboratory technical personnel have been required to spend considerable time in removing the individual hydra from the dishes, cleansing them in water and returning them to clean dishes. In a typical laboratory experiment, as many as 12 large finger-bowl type dishes of hydra may be required and several hours of time is required to take care of these. Moreover, such dishes are not particularly well adapted for the rapid reproduction and growth of hydra since they are not readily temperature controllable and require large volumes of fresh culture medium 4 or 5 times per week, since the medium tends to become stagnant if at rest in such dishes. Therefore, there has been a need in the art for more efficient hydra cultivation methods and apparatus. Moreover, since the hydra must be removed from the dishes for cleaning, which prevents a stable population from being formed, and causes adult hydra to be killed during transfer to clean bowls, a need exists for a method and apparatus for cleaning the hydra without removal from their environment.

OBJECTS OF THE INVENTION

It is therefore an object of the invention to provide an improved method whereby hydra can be grown.

A further object of the invention is to provide an apparatus for efficient growing of hydra.

A further object of the invention is to provide such an apparatus which comprises means for temperature control of the medium in which said hydra are grown.

A further object of this invention provides means for prevention of stagnation, such as aeration of the medium.

Still a further object of the invention is to provide a method whereby a population of hydra may be maintained substantially constant without the requirement of substantial supervision by technical personnel.

Still a further object of the invention is the simplification of the feeding of hydrozoa and efficient removal of non-ingested food and detritus of digestion without disturbing the growing hydrozoa.

SUMMARY OF THE INVENTION

The above objects of the invention and needs of the art are satisfied by the present invention which comprises a method and apparatus for the efficient growth of hydra. The apparatus comprises a long, flat, wide tank adapted at one end to receive a flow of water, increase its velocity while uniformly distributing it onto and over the bottom of the tank, and at the other end to provide a flow outlet, thus defining a flow path in the tank. A net may be disposed at the outlet of the tank such that loose hydra are collected on the net, while the mesh size is desirably such that any unconsumed food or debris passes through the net, thus allowing ready cleansing of the tank. Filtration and pumping apparatus are also provided as is water temperature regulation and aeration apparatus. The surface of the tank is desirably a plastic which has been roughened by, e.g., sanding, so as to provide a surface for the attachment of the hydra and facilitating their migration through the tank. In this way, the hydra continually reproduce by budding, stay attached to the substratum provided and migrate about. When it is necessary to provide a quantity of hydra for experimental purposes, they are detached by, for example, carefully "shaving" them from the surface. The current then carries them towards the net on which they are caught and from which they can be readily removed simply by tipping the net over.

BRIEF DESCRIPTION OF THE DRAWINGS

The invention will be better understood by referring to the accompanying drawings in which:

FIGS. 4a and 4b show the hydra in their relaxed state and when a current is being applied to the fluid medium within which they are grown.

DESCRIPTION OF THE PREFERRED EMBODIMENTS

Figure 1:
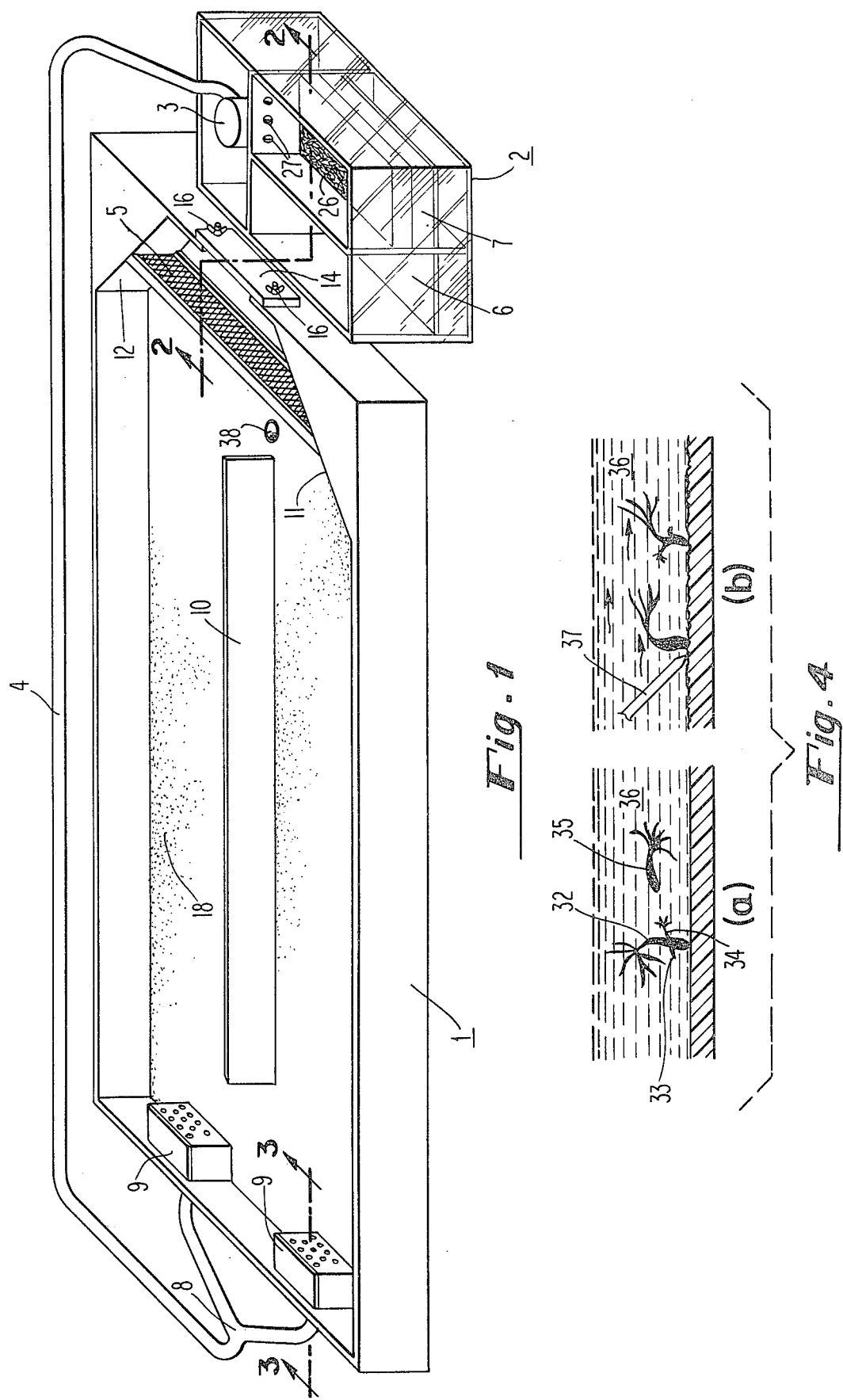
FIG. 1 represents an overall perspective schematic view of the apparatus of the invention.
Figure 2:
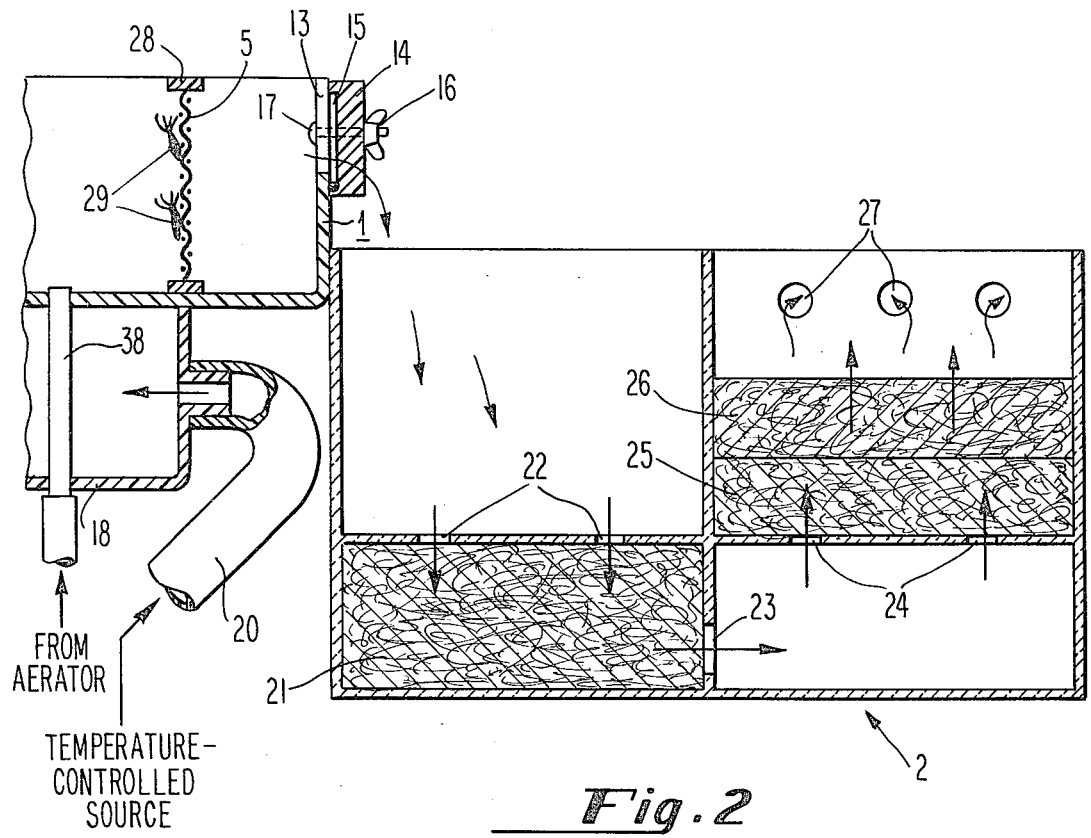
FIG. 2 represents a cross-sectional view taken along the line 2—2 of FIG. 1.
Figure 3:
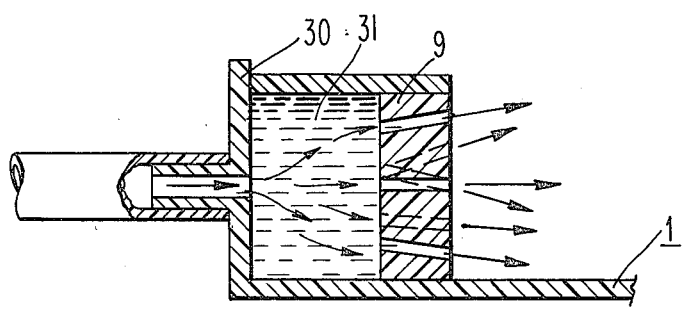
FIG. 3 represents a cross-sectional view of flow diversion means taken along the line 3—3 of FIG. 1.

Referring now to FIG. 1, an overall view of the system of the invention for growing hydra is shown. It comprises a tank 1, a filtering and pumping station 2, and a tube 4 connecting the tank 1 and a pump 3 for returning the fluid medium in which the hydra are grown to the tank 1. It is well known in the art that the optimum solution for growing hydra is one comprised largely of water and certain mineral salts such as calcium chloride. A suitable solution is an adaptation of that described by Loomis and Lenhoff in 1956 (Journal of Experimental Zoology, vol. 132, pages 555–573) containing a chelater to remove copper ions (Chalkley and Park, 1947, Science, vol. 105, page 553). Hydra are disposed for growth in the tank 1 and as is well known, over a period of three or four days, will reproduce asexually by budding if cared for properly. As discussed above, from time to time it is necessary to clean the medium in which the hydra are grown of uneaten food and other debris. For this reason, the pump 3 and filtration means 2 are provided. For example, once a day the pump may be run for approximately 20 minutes. This will repeatedly recycle all the aqueous medium through the filtration and pumping station 2 and all such debris and unused food will be passed through a screen 5 and be collected in filtration units 6 and 7. After this cleaning, the hydra may then be fed by sprinkling food on the surface of the medium. For example, live brine shrimp can be used provided they are washed in fresh water prior to being fed to the hydra inasmuch as the hydra do not respond well to the presence of sodium chloride salts in their medium. As shown in FIG. 1, the tube 4 carrying the solution from the pump 3 back to the tank 1 may be split in a conventional Y connector 8 and passed by additional tubes to flow diversion blocks 9. These blocks, which are described in further detail below in connection with FIG. 3, are drilled in differing directions so as to ensure that the flow is regular across the surface of the tank 1. Other flow regulation means could, of course, be used; for example, a dam could be used so as to provide an even spillway across the end of the tank 1 and to increase the flow velocity, by providing the water stored behind the dam with additional potential energy; a tube running crosswise of the tank 1 could be drilled at a plurality of locations and connected to the tube 4 to ensure even flow of the medium. Another possibility is to erect a wall in front of the inlets, so as to prevent all direct flow. The tank may also be divided by a center divider 10 in order to maintain, for example, differing age groups on one side or the other. Obviously multiple dividers could be used. Similarly, an option which is sometimes useful are flow barriers 11 and 12 which serve to direct the flow of water towards a smaller net area 5 thus concentrating it. A spillway 13 may be provided on the other side of the net to direct the flow into the filtration and pumping unit 2. The spillway may be provided as shown in FIG. 2 with a block 14 to prevent the passage of water therethrough except when the block 14 is removed. A gasket 15 may be provided, in conjunction with wing nut 16 and screw 17 to seal the block 14 against the surface of the tank 1.

In a preferred embodiment, the tank 1, the flow diverter blocks 9, the barriers 11 and 12, the divider 10 and the container for filtration and pumping units 2 are all fabricated of a plastic material non-toxic to the hydrozoa. Preferably this plastic is a clear material permitting uniform illumination and to enable ready examination of the conditions within the tank and may comprise the material known as "Lucite". Preferably, the floor of the tank 1 is roughened as shown diagrammatically at 18 in FIG. 1 by, e.g., sanding with number 220 grit sandpaper. This enables the hydra to get a better purchase on the Lucite surface of the tank 1, which in its unsanded state is a very smooth surface and hard to attach to. The desired surface finish, whether formed in Lucite by sanding with 220 grit paper or otherwise, is between about 8 and about 125 micro-inches average, specified in accordance with ASA B46.1-1955. Such a finish provides a good surface for attachment of hydra, but permits their ready detachment by a preferred method discussed in connection with FIG. 4 below. It is desirable that the hydra attach to the surface for several reasons. One is that if a given section of hydra is removed, as will be discussed below, the remaining hydra will tend to fill in the thus-denuded area, thus maintaining a stable population of substantially uniform density, which in useful in maintaining experimental continuity. A second reason, relating to the ease of detachment of the hydra from the surface when "harvest" is required, will be discussed in further detail below in connection with FIG. 4.

When a harvest is desired, the preferred procedure is, therefore, to turn on the pump 3, thus causing a current to flow through the tube 4 and flow diverters 9 and over the spillway 13, thus establishing a prevailing flow-left to right in FIG. 1. As discussed above, any extra food or debris will pass through the net or screen 5 and be filtered out of the medium by filtration means 6 and 7. The net 5, however, is sized so as to prevent the passage therethrough of hydra. If a quantity of hydra are detached from the surface of the tank, they will float downstream with the current but be caught on the net. The quantity of hydra harvested is thus dependent largely upon the length of time the pump is run and the amount of hydra which are detached from the surface. In this way, it is very simple to provide a harvest of as many hydra as desired. This is in clear distinction to the method of the prior art in which one was obliged to pick individual or small groups of hydra from a plain bowl or alternatively to filter them entirely from the media, which might be likely to cause them injury or death if not promptly returned to suitable media soon thereafter.

The second possible mode of harvesting is to keep the current flowing more or less continuously. When offspring are produced by the hydra, they will then, having specific gravity less than one, float to the surface of the water and be collected on the net. However, this offers the drawback that the current must be kept circulating constantly which will tend to lead to less efficient utilization of food since it will be swept away by the current very quickly before the hydra have a chance to capture and eat it. Therefore, the preferred mode of operation is to allow a substantially stable population of hydra to collect on the floor of the tank 1 and only remove them as necessary and then letting them be caught on the net 5. The net 5 may be provided with a frame whereby it may be simply picked out of the medium and inverted over a dish, the hydra then falling to the dish for use in whatever experiments may be desired.

Referring to FIG. 2, details of the construction of the tank and of the filtration means are shown. The tank 1 is shown as further comprising a temperature control chamber 18, which may be a second Lucite tank attached to the underside of the main tank 1. A hose 20 may be attached to the temperature control means 18 and water may be passed therethrough at the proper temperature for growth of a population of hydra. It is well known in the art that if the temperature is maintained at approximately 18° C., the hydra reproduce asexually. If the temperature deviates substantially from this, they tend to sexual reproduction, and by passing water of the proper temperature through the temperature control means 18, their mode of reproduction can be largely controlled. In a preferred embodiment, ordinary tapwater is passed through the temperature control means 18 which provides a suitable temperature for asexual reproduction. In a presently preferred embodiment, at least one tube 38 is arranged to pass completely through the temperature control chamber 18. One end of a conventional aquarium aerator (an air pump) may be attached to this tube, the other outletting into the medium. The aerator thus provides oxygenation and agitation to the medium and prevents stagnation.

When block 14 is removed by detaching wing nut 16 from screw 17, water is permitted to pass through the spillway 13 and falls into a first filtration region 21. This may comprise "Dacron" or glass fiber material. By making the filtration and pumping tank 2 out of Lucite, holes such as those indicated at 22, 23 and 24 may be provided to direct the flow of the water through the various filtration stages. For example, region 21 may, as explained above, be a Dacron material. A second filtration stage 25 may comprise activated charcoal in a cheesecloth bag or other suitable container, while a third filtration stage 26 may again be Dacron. Finally, outlet holes 27 are provided and are of a sufficient height above the bottom of the filtration unit 2 as to ensure substantial residence time therein and complete cleaning from the water of any uneaten food or other debris collected in the tank 1.

As shown in FIG. 2, the net 5 may comprise an ordinary piece of screen cemented or welded into a frame 28 for ready handling by laboratory personnel. Several hydra 29 are shown as having been collected on the net by the action of the current passing therethrough. These can be removed from the net simply by inverting the net 5 over a suitable bowl or dish and allowing them to fall off the net. In a presently preferred embodiment, the screen size is approximately 40 mesh. This allows the preferred food, brine shrimp, as well as debris to pass through the net, while catching hydra readily thereon.

Referring now to FIG. 3, a flow diverter arrangement is shown which provides for even flow in all directions. The medium is shown arriving at the left of the figure through a conventional hose and fitting attached by, e.g., cement to a wall 30 of the tank 1. A drilled flow direction block 9 is shown having a plurality of flow passages therethrough spreading outwardly from a plenum 31 thus enabling flow of the fluid medium in a plurality of directions. In this way, no one direction tends to predominate thus setting up an uneven current through the tank 1. As discussed above, a plurality of other methods of providing an even flow could be used such as, e.g., a dam, or a tube coming from one side of the tank 1 and being drilled with a number of holes providing steady fluid flow.

Referring now to FIGS. 4a and 4b, the hydra themselves are shown therein. In FIG. 4a, a first hydra 32 is shown comprising a body having a means for attachment to a surface of the tank 1 at its lower extremity and a plurality of tentacles at its other extremity. It is shown growing two young hydra asexually as buds. That indicated at 33 is a young, still embryonic hydra whereas hydra 34 is comparatively matured, exhibiting tentacles and being nearly ready for disconnection from the parent 32. A second hydra 35 is shown floating freely in the medium 36. In FIG. 4b, the surface of the tank 1 is shown as being comparatively roughened by, e.g. sanding, as discussed above and the hydra are shown attached to the roughened surface. A current is flowing, as indicated by the arrows in the medium 36, causing the hydra to be "leaned over" with the flow of current. A sharp blade 37, which may comprise an ordinary single edge razor blade, is shown as being about to detach the two hydra from the surface of the tank 1. If this is done carefully, the hydra can be removed from the tank, causing them to lodge in the net downstream, without substantial damage to their attaching regions.

It will be understood by those skilled in the art that there has been disclosed above a system and apparatus for economical and efficient growth of hydra. All the objectives of the invention and needs of the art are fulfilled inasmuch as the both hydra themselves and their tank are readily cleansed by the passage of water therethrough while the debris is filtered from the medium, thus allowing it to be recycled. Moreover, the number of hydra removed for an experiment can be readily controlled simply by varying the amount of area scraped by the blade to remove the hydra. Furthermore, operation of the system of the invention is very simple; the current merely need be turned on for a short period of time each day to clean the tank. It may be that more thorough cleaning of the tank 1 will be necessary from time to time, e.g. once per month. If so, all hydra can be detached as outlined above and transferred to a second tank while the first is being cleaned. The temperature control means and aeration means are desirably left in constant operation. If the hydra demand phototropic variation of light and dark, this can be readily arranged for by simply putting an opaque cover on the tank when it is desired that the hydra should be in darkness.

Moreover, it will be understood that while a preferred embodiment of the apparatus and method of the invention has been disclosed, there are numerous modifications and additions which can be made thereto without substantially departing from its scope. For example, in a preferred embodiment, the pump means is a Little Giant Pump Company model No. 1, which is an all-plastic submersible model emitting no toxic substance into the medium. The flow rate of this pump is approximately 200 gallons per hour, which is suitable for the practice of the process of the invention in a preferred embodiment, in which the tank is approximately 4 sq. ft. in extent. Similarly, while the use of a Lucite plastic for the tank and for containment of the filtering and pump means has been disclosed, clearly other materials could be used. However, it will be understood, of course, by those skilled in the art, that the material chosen must be, like Lucite, non-toxic to hydra. Likewise any glues or cements used to fasten the various components of the system together must likewise be non-toxic. It has been noted by the applicant that contact and "rubber" cements are toxic to hydra and their use should be accordingly avoided while epoxy and "Instant" cements are non-toxic and may be used in the fabrication of the apparatus of the invention.

Therefore, the above description of the invention should be construed as exemplary only and not as a limitation on its scope which is more properly defined by the following claims.

What is claimed is:

1. Method for growing hydrozoa which produce offspring having a specific gravity substantially equal to unity, comprising the steps of:
   providing a liquid medium consisting chiefly of water in which said hydrozoa can live and reproduce by budding;
   providing a wide, shallow, substantially elongated flat-bottomed tank having a roughened bottom surface for containing said medium;

establishing an initial population of hydrozoa in said medium;
periodically feeding said hydrozoa;
permitting said offspring to float to the surface of said medium; and
providing a current in said medium from a source at one of said tank to overflow means at the other for collecting said offspring on a net disposed in said current.

2. The method of claim 1 wherein a substantially constant resident population of said hydrozoa remains substantially fixed in said medium for continuous production of said offspring.

3. The method of claim 1 wherein said current in said medium is used to collect said offspring on net means, said current being of low velocity such that said offspring are undamaged by collection on said net means.

4. The method of claim 3 wherein said medium is recycled through filtering means and the current of said recycling is used to collect said offspring on said net means.

5. Method for production of hydrozoa, comprising the steps of:
providing a shallow, elongated residence tank, having a flat, roughened bottom surface for the attachment of hydrozoa;
filling said tank with a liquid medium suited to the growth of said hydrozoa;
permitting a resident population of hydrozoa to be established on said surface;
periodically feeding said population;
permitting the members of said population to asexually reproduce; and
collecting the offspring of said reproduction by establishing a current from one end of said tank to another, whereby said offspring are collected on net means upstream of a spillway, and said offspring are not damaged by collection.

6. The method of claim 5 wherein said offspring have a specific gravity less than that of said medium.

7. The method of claim 5 wherein said medium is recycled and filtered.

8. The method of claim 7 wherein said filtration step is performed on activated charcoal.

9. Apparatus for the production of living hydrozoa, comprising:
a shallow, comparatively wide tank for the containment of an aqueous medium conducive to the growth of said hydrozoa, and having a substantially horizontal, planar bottom surface, said surface being roughened as by sanding for the attachment thereto of a population of hydrozoa;
pump means for recycling said medium for filtration purposes, the inlet of said pump being connected to a spillway at a first end of said tank and its outlet being connected to the opposing end of said tank, the capacity of said pump means being chosen in relation to the size of said tank such that a gentle, sheet-like flow of said medium through said tank is obtained, whereby a flow path is established in said medium; and
net means disposed in said flow path for collecting detached ones of said population, the rate of said flow being low, so that said detached ones are not damaged by said collection.

10. The apparatus of claim 9 further comprising means for oxygenation of said medium.

11. The apparatus of claim 9 wherein the specific gravity of said hydrozoa can be less than that of said medium.

12. The apparatus of claim 9 wherein the mesh size of said net is substantially −40 mesh.

13. The apparatus of claim 9 wherein said hydrozoa are hydra.

14. The apparatus of claim 9 further comprising means for ensuring that said flow path is regular.

15. The apparatus of claim 9 wherein said surface is of plastic, having been roughened.

16. The apparatus of claim 9 wherein the apertures is said net means are so sized as to permit the passage therethrough of excess food and other debris carried by said medium, but not of said hydrozoa.

17. The apparatus of claim 16 further comprising means for maintenance of the temperature of said medium within said tank.

18. The apparatus of claim 16 further comprising filtration means disposed in said flow path for removal of said excess food and other debris from said medium.

19. The apparatus of claim 18 wherein said filtration means comprises activated charcoal.

20. The apparatus of claim 9 wherein said medium consists essentially of water and selected mineral salts.

21. The apparatus of claim 20 wherein said mineral salts comprise CaCl.

22. A method for the growing of hydrozoa, comprising the steps of:
providing a tank having a surface therein adapted for the attachment of hydrozoa thereto;
providing an aqueous medium comprising water and mineral salts in said tank;
periodically feeding said hydrozoa;
periodically pumping said medium through filtration means for cleansing thereof;
maintaining said medium at a temperature suitable for the growth of said hydrozoa; and
periodically harvesting said hydrozoa wherein said harvesting step comprises the steps of:
providing a current in said medium, whereby said hydrozoa are similarly oriented with respect to said current;
causing a quantity of said hydrozoa to be detached from said surface; and
collecting said detached hydrozoa on means disposed downstream of their point of detachment.

23. The method of claim 22 wherein said current is provided by the means used for said pumping step.

24. The method of claim 22 wherein said harvesting step is performed during said pumping step.

25. The method of claim 22 wherein said hydrozoa are caused to be detached by passing a sharp blade between said hydrozoa and said surface.

26. The method of claim 22 wherein said hydrozoa are hydra.

27. The method of claim 22 comprising the step of oxygenation of said aqueous medium.

28. The method of claim 22 wherein said surface for attachment comprises a plastic having been roughened.

29. The method of claim 22 wherein said surface adapted for the attachment of hydrozoa is adapted therefor by being sufficiently rough that said hydra can attach themselves thereto.

30. The method of claim 29 wherein said surface is made sufficiently rough by sanding.

31. The method of claim 30 wherein said sanding step is performed with 220 grit sandpaper.

32. The method of either of claims 28 or 31 wherein said surface is roughened to a finish between about 8 and about 125 microinches average peak to valley distance.

* * * * *